US012779130B2

(12) United States Patent
Wilczek et al.

(10) Patent No.: US 12,779,130 B2
(45) Date of Patent: Nov. 3, 2026

(54) DRIVE MECHANISM FOR AN APPLICATOR FOR DELIVERING A DOSE OF MEDICAMENT AND A CORRESPONDING APPLICATOR

(71) Applicant: NEMERA SZCZECIN SPOLKA Z OGRANICZONA ODPOWIEDZIALNOSCIA, Szczecin (PL)

(72) Inventors: Mateusz Wilczek, Szczecin (PL); Arkadiusz Lukasz Woitas, Szczecin (PL); Alberto Lozano Platonoff, Szczecin (PL)

(73) Assignee: NEMERA SZCZECIN SPOLKA Z OGRANICZONA ODPOWIEDZIALNOSCIA, Szczecin (PL)

( * ) Notice: Subject to any disclaimer, the term of this patent is extended or adjusted under 35 U.S.C. 154(b) by 912 days.

(21) Appl. No.: 18/001,816

(22) PCT Filed: Jun. 16, 2021

(86) PCT No.: PCT/IB2021/055308
§ 371 (c)(1),
(2) Date: Dec. 14, 2022

(87) PCT Pub. No.: WO2021/255663
PCT Pub. Date: Dec. 23, 2021

(65) Prior Publication Data
US 2023/0226282 A1 Jul. 20, 2023

(30) Foreign Application Priority Data
Jun. 17, 2020 (PL) ...................................... P434361

(51) Int. Cl.
*A61M 5/315* (2006.01)

(52) U.S. Cl.
CPC .... *A61M 5/31585* (2013.01); *A61M 5/31511* (2013.01); *A61M 5/31536* (2013.01); *A61M 5/31551* (2013.01)

(58) Field of Classification Search
CPC .......... A61M 5/31585; A61M 5/31511; A61M 5/31536; A61M 5/31551; A61M 2005/31518; A61M 5/31541
See application file for complete search history.

(56) References Cited

U.S. PATENT DOCUMENTS 5,226,895 A * 7/1993 Harris ............... A61M 5/31591 604/218
6,004,297 A 12/1999 Steenfeldt-Jensen et al.
(Continued)

FOREIGN PATENT DOCUMENTS

CN 1835774 A 9/2006
CN 105705181 A 6/2016
(Continued)

*Primary Examiner* — Lauren P Farrar
(74) *Attorney, Agent, or Firm* — FisherBroyles, LLP; Ronni S. Jillions

(57) ABSTRACT

An applicator and a drive mechanism for the applicator for delivering a dose of a medicament, wherein when a dose is set by the knob, the clutch element is rotated so that the drive spring is loaded, while the drive element and the piston rod are immobilized, and when the dose is delivered, the drive spring is released causing the drive element to rotate together with the piston rod, the piston rod moving axially in a distal direction, the shaft being rotatably engaged with the clutch element so that during the setting of each subsequent dose the shaft is rotated in relation to the piston rod and moved axially in a proximal direction, while during the delivery of the dose the shaft is immobilized in relation to the piston rod, and wherein the total translation of the shaft in relation to the piston rod caused by the setting of a defined number of doses is limited by blocking elements located respectively on the piston rod and the shaft.

13 Claims, 10 Drawing Sheets

(56) References Cited

U.S. PATENT DOCUMENTS

| | | | | |
|---|---|---|---|---|
| 9,358,343 | B2 | 6/2016 | Wieselblad et al. | |
| 10,300,206 | B2 | 5/2019 | Bergens et al. | |
| 2001/0031945 | A1* | 10/2001 | Haar | A61M 5/30 604/134 |
| 2006/0206057 | A1* | 9/2006 | DeRuntz | A61M 5/31551 604/224 |
| 2014/0236097 | A1 | 8/2014 | Jugl et al. | |
| 2017/0296754 | A1 | 10/2017 | Avery et al. | |
| 2017/0304551 | A1 | 10/2017 | Eardley et al. | |
| 2017/0312441 | A1 | 11/2017 | Draper et al. | |
| 2019/0015595 | A1 | 1/2019 | Keitel | |
| 2019/0366009 | A1* | 12/2019 | Hewson | A61M 5/31593 |

FOREIGN PATENT DOCUMENTS

| | | | |
|---|---|---|---|
| CN | 106999667 | A | 8/2017 |
| EP | 0338806 | B1 | 2/1994 |
| EP | 2829292 | A1 | 1/2015 |
| EP | 2814547 | B1 | 7/2015 |
| WO | 9938554 | A1 | 8/1999 |
| WO | 0119434 | A1 | 3/2001 |
| WO | 2007017053 | A1 | 2/2007 |
| WO | 2010089418 | A2 | 8/2010 |
| WO | 2010149209 | A1 | 12/2010 |
| WO | 2013119132 | A1 | 8/2013 |
| WO | 2013156345 | A2 | 10/2013 |
| WO | 2016041883 | A1 | 3/2016 |
| WO | 2016146448 | A1 | 9/2016 |
| WO | 2017064275 | A1 | 4/2017 |
| WO | 2017098460 | A1 | 6/2017 |
| WO | 2017134131 | A1 | 8/2017 |
| WO | 2018007259 | A2 | 1/2018 |

* cited by examiner

DRIVE MECHANISM FOR AN APPLICATOR FOR DELIVERING A DOSE OF MEDICAMENT AND A CORRESPONDING APPLICATOR

The present application relates to a drive mechanism for an applicator for delivering a dose of a medicament and a corresponding applicator, in particular a drive mechanism and an applicator provided with a last dose blocking. Devices for delivering multiple doses of a medicament by subcutaneous injection in which the volume of a dose may be pre-selected are known in the art. They usually comprise a housing comprising a mechanism for axial translation of a piston rod and a cartridge enclosure adapted to receive a medicament cartridge. In the cartridge a piston is located the translation of which by means of the piston rod causes a suitable dose of medicament to be pushed out of the cartridge. Such applicators are especially useful for patients who need to receive medication doses on regular basis, in particular adjustable medication doses.

Such an applicator is described for example in the international application WO99/38554A1. Here, the force needed for translating the piston rod is exerted directly by a user by pressing a button. Alternatively, the force needed for translating the piston rod may by exerted by a spring which is preferably loaded by a user, as in the applicators known from the documents EP0338806B1, WO2010/089418A2 or WO2017/064275A1.

In the applicators for delivering adjustable doses of medicament it is essential to prevent the possibility of setting a dose that is larger than a volume of a medicament remaining in a cartridge. Without such provision there is a risk that the dose delivered by the applicator will be smaller than the required dose set by a user. Such mechanisms are disclosed for example in WO01/19434A1 describing a setting mechanism including coaxial cylinders with a sleeve being translated therebetween towards a final position in which the sleeve abuts a blocking element when the set dose equals the dose remaining in the cartridge. In a similar mechanism known from WO2010/149209A1 a spherical element is used instead of an annular sleeve. European patent EP2814547B1 describes a last dose limiting mechanism in which blocking elements are moved along closed path curves, the shape of the curves as well as the speed of the blocking elements moving along them are so adjusted that the blocking elements contact each other upon delivery of a last dose.

The aim of the currently disclosed solution was to provide a drive mechanism with last dose blocking, for an automatic applicator allowing for precise setting and preferably also correcting of a dose of a medicament. A particular aim was to provide a blocking mechanism preventing the possibility of setting a dose larger than the volume of the medicament in a cartridge.

Further, the aim was to provide a reliable last dose blocking that would not require any essential modifications of the setting mechanism and other elements of the applicator, in order to reduce costs and facilitate manufacturing of the applicator.

The aim was also to create a last dose blocking that could be used in a handy compact-size applicator. Another aim was to design an automatic applicator with a replaceable cartridge, the applicator being equipped with a drive mechanism with a last dose blocking, enabling precise setting and correcting of a dose of a medicament.

According to the above aims a drive mechanism for an applicator for delivering a dose of a medicament, is provided comprising:

a dose setting assembly, a knob, a rotatable and axially non-translatable clutch element coupled in rotation with the knob and cooperating with the dose setting assembly, a rotatable piston rod having an external thread, the piston rod being located inside the clutch element, a drive element and a drive spring, wherein when a dose is being set by means of the knob, the clutch element is rotated so that the drive spring is loaded, while the drive element and the piston rod are immobilized, and when the dose is being delivered, the drive spring is being released causing the drive element to rotate together with the piston rod, the piston rod being translated axially in a distal direction, wherein the piston rod is hollow and has an internal thread, and a shaft having an external thread for cooperation with the internal thread of the piston rod is located within the piston rod, the shaft being coupled in rotation with the clutch element so that during the setting of each subsequent dose the shaft is rotated in relation to the piston rod and translated axially in a proximal direction, while during the delivery of the dose the shaft is immobilized in relation to the piston rod, and wherein the total translation of the shaft in relation to the piston rod caused by the setting of a defined number of doses is limited by means of blocking elements located respectively on the piston rod and the shaft.

Preferably, the shaft is coupled in rotation with the clutch element by means of longitudinal splines.

The blocking elements may comprise a projection located on the internal thread of the piston rod and a projection located on the external thread of the shaft, the blocking elements being adapted to block the rotation of the piston rod in relation to the shaft.

Preferably, the drive element has an orifice of a non-circular cross-section, the piston rod has a cross-section with a non-circular contour corresponding to the non-circular cross-section of the orifice of the drive element.

An applicator for delivering a dose of a medicament, is also provided comprising:

a housing, a cartridge enclosure adapted to receive a medicament containing cartridge, a dose setting assembly, a knob, a rotatable and axially non-translatable clutch element coupled in rotation with the knob and cooperating with the dose setting assembly, a rotatable piston rod having an external thread, the piston rod being located inside the clutch element, a drive element and a drive spring, wherein when a dose is being set by means of the knob, the clutch element is rotated so that the drive spring is loaded, while the drive element and the piston rod are immobilized, and when the dose is being delivered, the drive spring is being released causing the drive element to rotate together with the piston rod, the piston rod being translated axially in a distal direction, wherein the piston rod is hollow and has an internal thread and a shaft having an external thread for cooperation with the internal thread of the piston rod is located within the piston rod, the shaft being engaged in rotation with the clutch element so that during the setting of each subsequent dose the shaft is rotated in relation to the piston rod and translated axially in a proximal direction, while during the delivery of the dose the shaft is immobilized in relation to the piston rod, and wherein the total translation of the shaft in relation to the piston rod caused by the setting of a defined number of doses is limited by means of blocking elements located respectively on the piston rod and the shaft.

Preferably, the drive element has an orifice of a non-circular cross-section, the piston rod has a cross-section with a non-circular contour corresponding to the non-circular cross-section of the orifice of the drive element.

Preferably, the drive element is releasably coupled with the dose setting assembly.

The blocking elements preferably comprise a projection located on the internal thread of the piston rod and a projection located on the external thread of the shaft, the blocking elements being adapted to block the rotation of the piston rod in relation to the shaft.

The applicator may comprise an indication mechanism comprising a control sleeve, a scale sleeve and a control nut, the control sleeve having an external thread for cooperation with the control nut, the control nut being blocked against rotation in the housing and axially translatable therein, and the control nut being also axially engaged with the scale sleeve, which is moved along a spiral path during the dose setting and the dose correcting.

Preferably, the indication mechanism comprises an indication window showing the currently set dose.

Preferably, the drive spring is a torsional spring.

The applicator preferably comprises a release mechanism adapted to be in a locked state or in an unlocked state, the release mechanism comprising an external activating element, wherein when the release mechanism is in the locked state, the drive element cannot rotate, and when the release mechanism is in the unlocked state, the drive element may rotate, the release mechanism being adapted to be switched from the locked state to the unlocked state by a user.

The external activating element may comprise a trigger located on a side wall of the housing, the trigger being blocked against rotation and axially translatable.

Preferred embodiments are shown in the drawings in which.

Figure 4A:
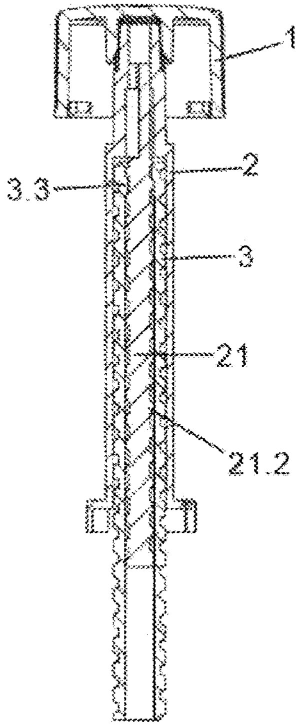
Figure 4B:
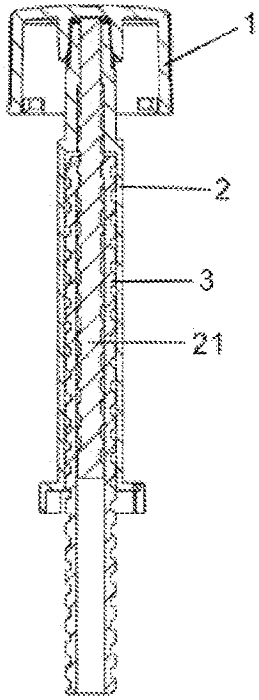
Figure 4C:
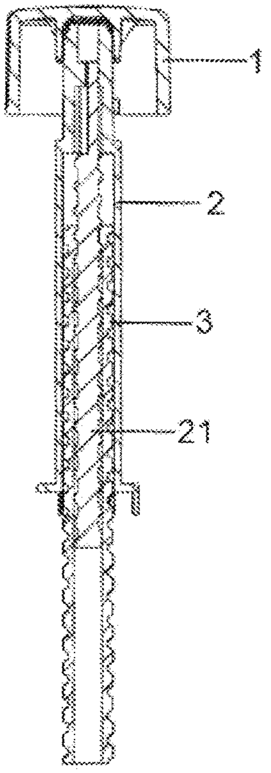
Figure 5A:
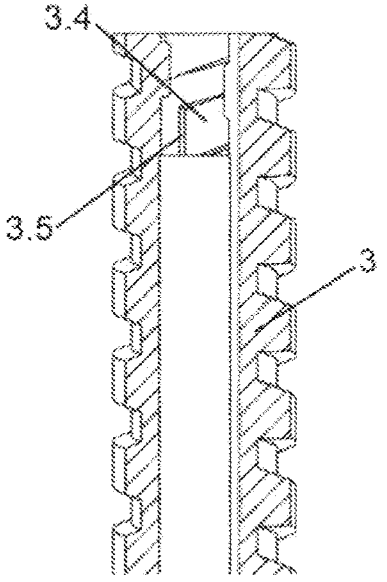
Figure 5B:
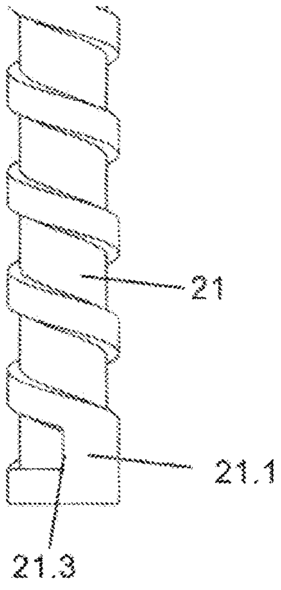
Figure 5C:
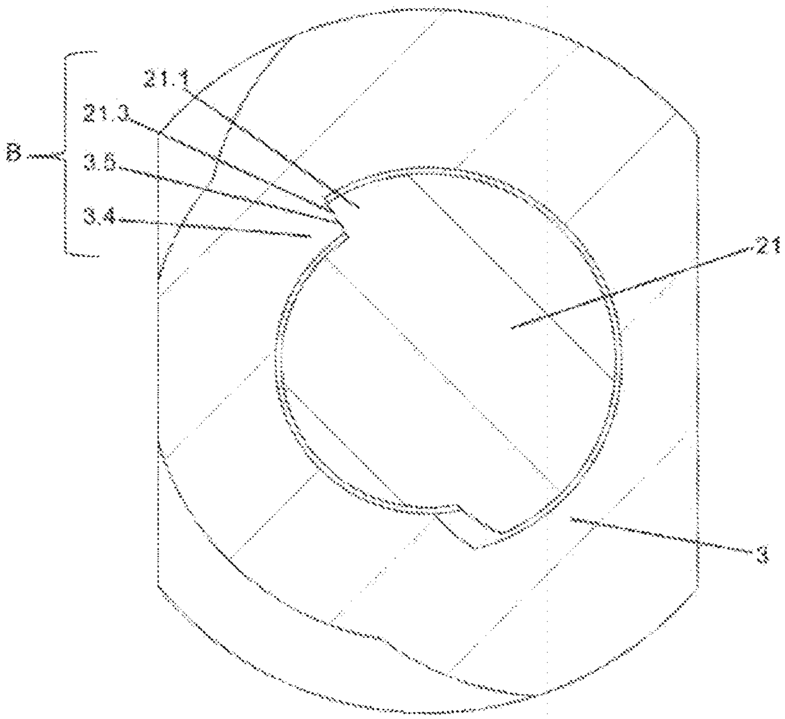
Figure 6:
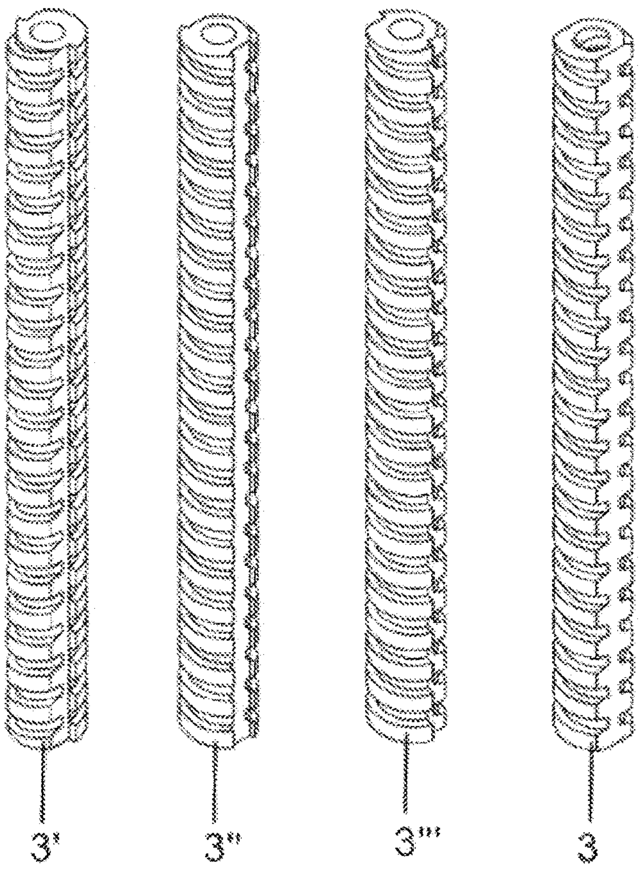
Figure 7:
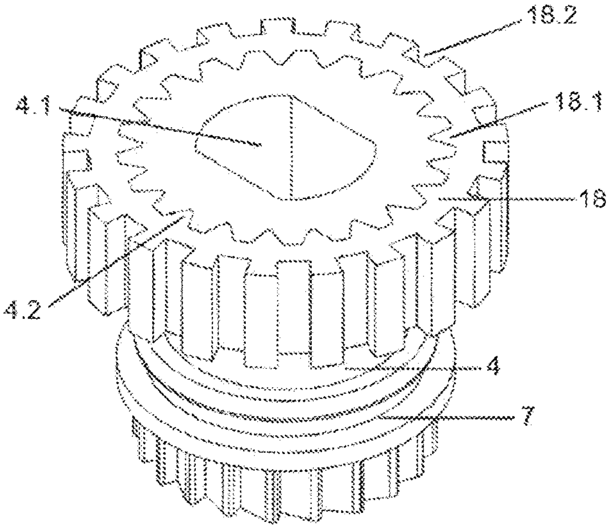
Figure 8A:
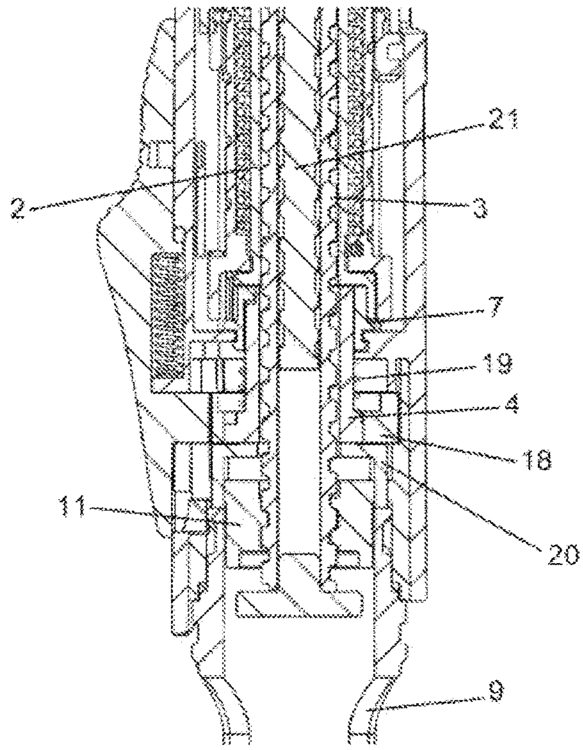
Figure 8B:
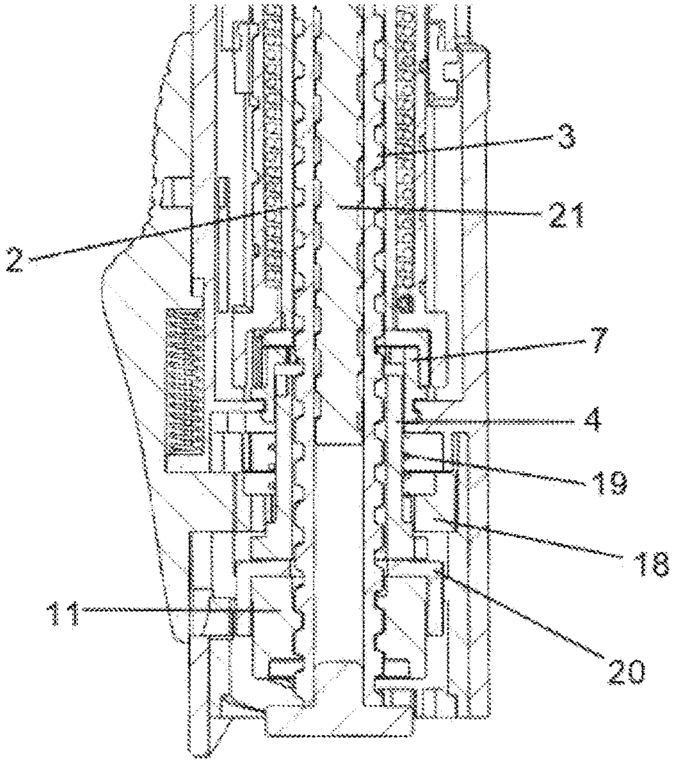
Figure 9:
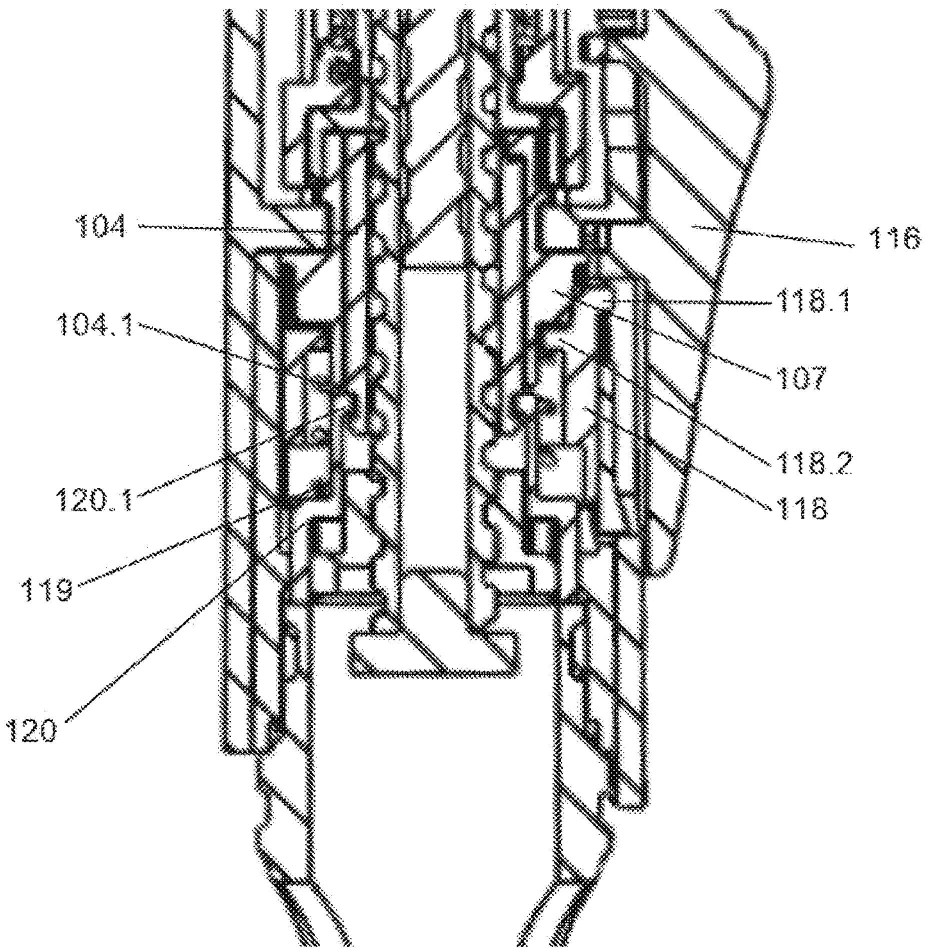
Figure 10:
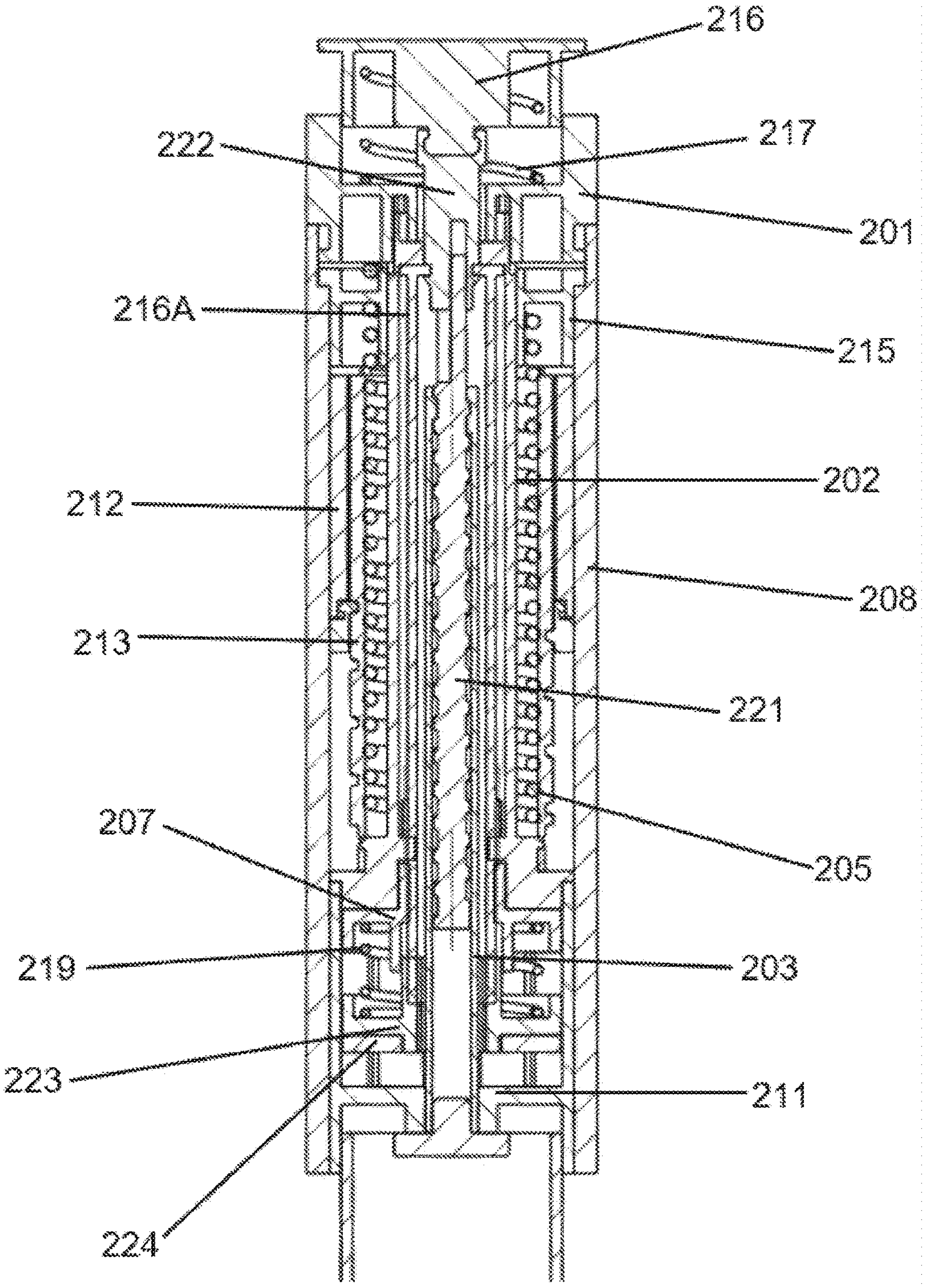

FIGS. 4*a*-4*c* illustrate the operation of a last dose blocking;

FIGS. 5*a*-5*c* show blocking elements;

FIG. 6 shows various cross-sections of a piston rod to be used in the applicator;

FIG. 7 shows a perspective view of the connection of a drive element with a blocking ring and a toothed ring;

FIGS. 8*a* and 8*b* show respective cross-sections of the applicator when its housing is connected with a cartridge enclosure and when the housing is disconnected from the cartridge enclosure;

FIG. 9 shows a longitudinal section of a fragment of an alternative automatic applicator provided with the disclosed drive mechanism;

FIG. 10 shows a longitudinal section of still another embodiment of the automatic applicator provided with the disclosed drive mechanism.

In the following description of embodiments a distal direction defines the direction towards an injection site and a proximal direction defines the direction towards a dose selection knob.

Figure 1:
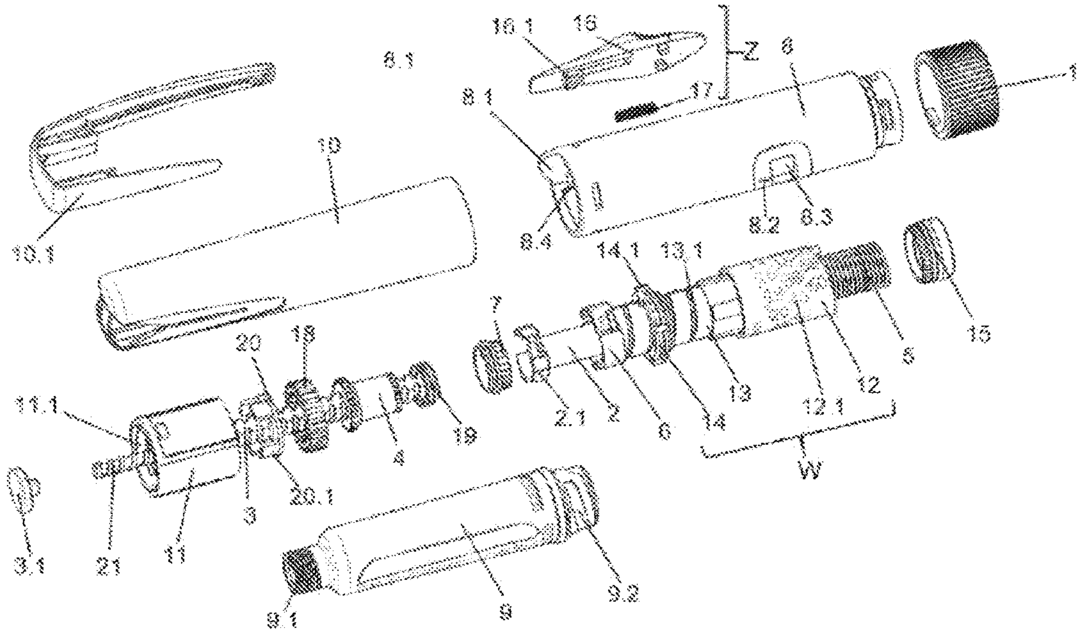
FIG. 1 shows an exploded view of an exemplary automatic applicator provided with the disclosed drive mechanism.
Figure 2:
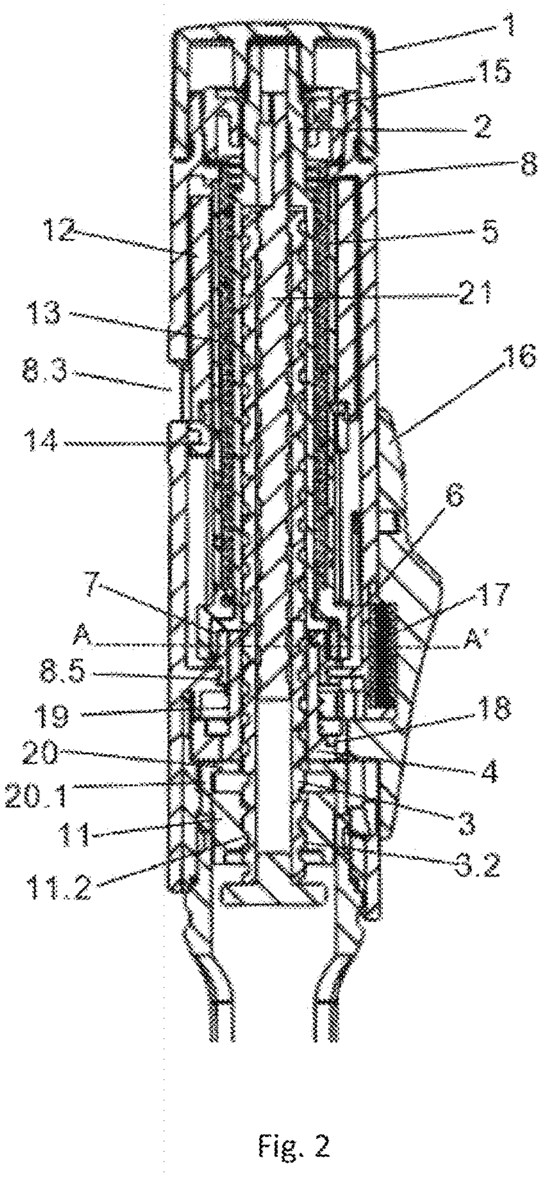
FIG. 2 shows a longitudinal section of a fragment of an exemplary automatic applicator provided with the disclosed drive mechanism.

The exemplary automatic applicator shown in FIGS. 1 and 2 is designed for delivering doses of a medicament the volume of which may be set and corrected before an injection. The mechanism for dose setting and dose correcting is similar to that described in WO2010/089418A2. Alternatively, other known in the art setting assemblies may be used, enabling to increase and to correct a dose and being driven by a control element rotationally coupled to or integral with a dose selection knob. In particular the alternative setting assemblies may comprise ratchet, tooth or ratchet-tooth mechanisms known in the art.

The applicator is provided with the disclosed drive mechanism. This mechanism comprises a dose setting assembly N, a knob 1, a rotatable and axially non-translatable clutch element 2, coupled in rotation with the knob 1 and cooperating with the dose setting assembly N. Preferably, the clutch element 2 is coupled with the knob 1 at its proximal end and it cooperates with the dose setting assembly N at its distal end. The mechanism further comprises a rotatable piston rod 3 located inside the clutch element 2, a drive element 4 and a drive spring 5.

The dose selection knob 1 is located at the proximal end of the applicator. The knob 1 is connected with the clutch element 2 via the splines or another connection ensuring coupling of these elements in rotational movement. In the described embodiment the knob 1 and the clutch element 2 may be rotated but their axial position is fixed.

Figure 3:
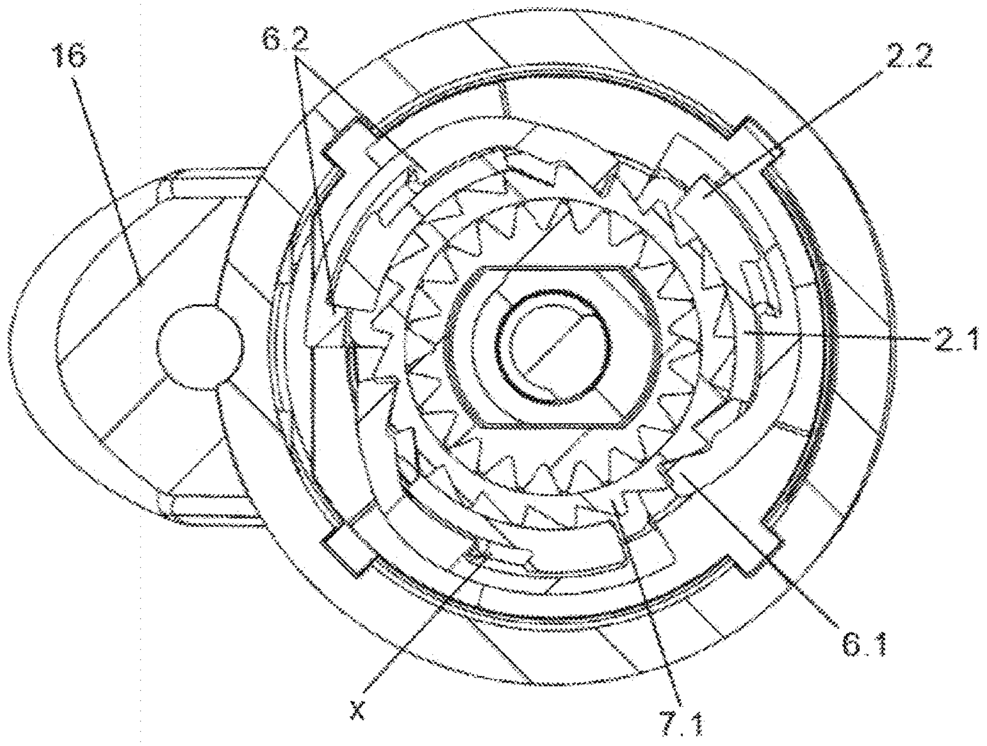
FIG. 3 shows a cross-section A-A' of a dose setting assembly.

At the distal end of the clutch element 2 arms 2.1 are located, the arms 2.1 being engaged with the dose setting assembly N. A cross-section A-A' of an exemplary dose setting assembly is shown in FIG. 3. In the described exemplary applicator, the dose setting assembly N comprises a ratchet element 6 (shown also in FIGS. 1-2). The ratchet element 6 surrounds the arms 2.1 of the clutch element 2 and a toother ring 7. The toothed ring 7 is located at least partially inside the ratchet element 6.

As mentioned above, the disclosed drive mechanism comprises among others the rotatable piston rod 3, the drive element 4 and the drive spring 5. As shown in FIG. 1, the drive element 4 is connected with the piston rod 3 via a non-circular contour of the piston rod 3 and a corresponding orifice 4.1 (shown in FIGS. 3 and 7) in the drive element 4. At the end of the piston rod 3 a piston rod ending 3.1 is located, for increasing a contact surface with a cartridge piston. In an alternative embodiment, the piston rod ending 3.1 may constitute and integral part of the piston rod.

The piston rod 3 may consist of a unitary element or it may by comprised of two or more parts connected in such a way that they are fixed to each other. Said parts may be interconnected axially or coaxially. Further, the piston rod 3 or its components may be made of polymer or metal. In the piston rod 3 consisting of more than one component all the components may be made of the same material or of different materials.

Referring still to FIGS. 1 and 2, the applicator described in this embodiment has also a housing 8 to be connected with a cartridge enclosure 9. Once the housing 8 has been connected with the cartridge enclosure 9, these two elements are rotationally and axially fixed in relation to each other. Preferably, the cartridge enclosure 9 may be detachable from the housing 8 in order to enable replacement of the medicament cartridge. Alternatively, in the case of a disposable applicator, said elements may be connected with each other during assembly in a non-releasable way. The applicator may be equipped with a cap 10 covering the distal end of the cartridge enclosure 9 when placed on the housing 8. A thread 9.1 is formed on said distal end for mounting a needle module comprising a needle through which the medicament contained in the cartridge flows. In the disclosed embodiment the cartridge enclosure 9 is connected with the housing 8 via a nut 11 shown in FIG. 11 having a projection 11.1 cooperating with a groove 9.2. However, these elements may also be snap-connected. In the described applicator, the housing 8 has a projection 8.1 allowing the cap 10 to be placed in just one fixed angular position. The cap 10 may be provided with a clip 10.1 facilitating the use of the applicator, e.g. enabling it to be attached to clothes.

In a preferred embodiment the piston rod 3 rotates in the nut 11. The piston rod 3 has an external thread 3.2 cooperating with a thread 11.2 of the nut (see FIG. 2), the nut 11 being rotationally and axially blocked in the housing 8. In an alternative variant, the piston rod 3 cooperates with a thread located directly on an integral element of the housing, preferably on an element facing towards the inside of the housing. The applicator according to this embodiment has also an indication mechanism W, indicating to the user the volume of a currently set dose. The indication mechanism W comprises a control sleeve 13, a scale sleeve 12 and a control nut 14. The volume of the dose is indicated by means of a numerical scale 12.1 located on the scale sleeve 12. When the dose is being increased, the scale sleeve 12 is being moved along a spiral path and subsequent numbers of the scale 12.1 are indicated by a marker 8.2 and appear in an indication window 8.3 which may be provided with a transparent cover and additional means improving visibility of the set dose, e.g. a lens. The scale sleeve 12 is rotationally coupled with the control sleeve 13, which in this embodiment is formed integrally with the ratchet element 6. In an alternative variant the ratchet element 6 may be a separate component that is rotationally coupled with the control sleeve 13. As shown in FIG. 1, the control sleeve 13 has a thread 13.1 on its external surface, the thread 13.1 cooperating with the control nut 14 provided with an internal thread. The control nut 14 is axially engaged with the scale sleeve 12 by means of e.g. clips; it is also blocked against rotational movement by means of projections 14.1 movable in longitudinal grooves 8.4 of the housing.

In FIG. 2 the drive spring 5 is shown, constituting a part of the drive mechanism of the disclosed applicator, the drive spring 5 being connected at one end to the control sleeve 13 and at the other end being fixed in a spring blocking 15 which is fixed in the housing 8. Other ways of mounting the drive spring 5 are also possible, for example it may be connected at one end to the ratchet element 6 or the clutch element 2. The other end of the drive spring 5 may also be fixed directly in the housing 8.

The applicator has also a release mechanism Z, allowing to block against rotation at least one element of the dose setting assembly or the drive element. Due to this mechanism, the energy accumulated in the loaded drive spring 5 is not immediately released back. When the release mechanism Z becomes unlocked, said at least one element of the dose setting assembly or said drive element is also unlocked, which allows the energy accumulated in the loaded drive spring to be released and the injection to be triggered. In this embodiment, the release mechanism Z comprises an external activating element 16 adapted to release the injection, the activating element 16 being axially translatable in the housing 8. The release mechanism Z is shown in detail in FIGS. 2 and 8*b*. It further comprises a spring 17 located between the activating element 16 and the housing 8. The external activating element 16 is connected to the drive element 4 by means of a blocking ring 18 shown in detail in FIG. 7. On the external surface of the blocking ring 18 projections 18.1 are provided for cooperation with corresponding indents 4.2 of the drive element 4. Other shapes of the cooperating surfaces 18.1 and 4.2 are possible provided that they ensure rotational coupling of the blocking ring 18 with the drive element 4. Said coupling may be releasable in the case of the applicator having a replaceable cartridge. The blocking ring 18 has also peripheral grooves 18.2 adapted to block the blocking ring 18 via a projection 16.1 located on the external activating element 16, in this embodiment in the form of a trigger.

Alternatively, the external activating element 16 may be located at the proximal end of the applicator. It may then have a form of a button separate from the dose selection knob 1 or the knob 1 itself may constitute an external activating element, being preferably releasable from the dose setting assembly N during injection.

A bearing 8.5 is shown in FIG. 2, enabling rotation of the drive element 4. In the illustrated embodiment said bearing is integral with the housing 8. Alternatively the bearing may be formed on a separate component fixed in the housing. Between the drive element 4 and the toothed ring 7 or the bearing 8.5 there is a spring 19 allowing to disconnect these elements in order to replace the medicament cartridge. There is a pushrod 20 having projections 20.1 on its distal side, abutting the drive element 4 on its proximal side. When the housing 8 is connected with the cartridge enclosure 9, the pushrod 20 contacts the cartridge enclosure 9 via said projections 20.1.

FIG. 3 shows a cross-section of the applicator along a plane A-A' indicated in FIG. 2, where the dose setting assembly N is shown.

The ratchet element 6 has external elastic arms 6.1 with projections 6.2, the arms 2.1 of the clutch element 2 having internal projections 2.2. The toothed ring 7 has circumferential teeth 7.1 to be seen in FIG. 3, on which the arms 6.1 of the ratchet element 6 rest. Between the projections 6.2 and the projections 2.2 of the clutch element 2 there is a play X allowing for rotation of these elements in a limited range. The position of the arms 6.1 on the toothed ring 7 corresponds to the currently set dose.

As may be seen in particular in FIGS. 4*a*-4*c* and 5*a*-5*c*, inside the piston rod 3 there is a threaded shaft 21 cooperating with an external thread, preferably a track 3.3, provided on the internal surface of the piston rod 3. The shaft 21 is rotationally engaged with the clutch element 2, e.g. via the splines or another connection ensuring blocking of relative rotation between these elements.

FIGS. 4*a*-4*c* illustrate how the last dose is blocked. FIG. 4*a* shows mutual positions of the applicator components before a dose is set. The knob 1 is rotationally coupled with the clutch element 2 which in turn is rotationally coupled with the shaft 21. In the disclosed embodiment both couplings are of the splines type but other known types of connections may be used, as e.g. any corresponding indents and projections on cooperating elements. FIG. 4*b* shows mutual positions of the applicator components after a dose has been set, and FIG. 4*c*—after the injection.

FIGS. 5*a*, 5*b* and 5*c* show the blocking elements B comprising blocking projections 3.4 located on the piston rod 3 and blocking projections 21.1 located on the shaft 21.

The blocking projections 3.4 have blocking surfaces 3.5 and the blocking projections 21.1 have blocking surfaces 21.3. When a dose is set that is equal to the volume of the medicament remaining in the cartridge, the blocking surfaces 3.5 contact the blocking surfaces 21.3 preventing further relative rotation between the piston rod 3 and the shaft 21.

FIG. 6 shows various embodiments of the non-circular cross-section of the piston rod 3 cooperating with the non-circular cross-section of the drive element 4.

FIG. 7 shows a perspective view of the connection between the drive element 4, the blocking ring 18 and the toothed ring 7. The figure shows a non-circular cross-section of the orifice 4.1 in the drive element 4 through which the piston rod 3 passes. In alternative variants, the orifice 4.1 may have a different cross-section, e.g. corresponding to the shapes of the piston rod 3 cross-sections shown in FIG. 6.

FIG. 8*a* shows a longitudinal section of a fragment of the applicator ready for use. The drive element 4 is connected to the toothed ring 7 and to the blocking ring 18 so that they may rotate together. The spring 19 is compressed and the cartridge enclosure 9 contacts the pushrod 20. FIG. 8*b* shows the same section in the case of the variant of a replaceable cartridge, after the housing 8 has been disconnected from the cartridge enclosure 9. The spring 19 is not compressed anymore and the drive element 4 is disconnected from the blocking ring 18 and the toothed ring 7.

Operation of the applicator provided with the drive mechanism according to the described preferred embodiment will now be described with reference to the above described figures.

In order to increase or correct a dose, the user rotates the knob 1 in one of the two directions. The clutch element 2 is rotated by means of the knob 1, hence the ratchet element 6 rotates as well due to the cooperation of the projections 2.2 and 6.2. In consequence of this rotation the elastic arms 6.1 of the ratchet element 6 pass subsequent teeth 7.1 of the toothed ring 7. The passage to a subsequent position on the toothed ring corresponds to a unitary increase of the dose volume, which is defined by the size of the toothed ring 7. The arms of the ratchet element 6 cooperate with the arms of the clutch element 2 via said projections 2.2 and 6.2 of the respective arms in such a way that when the arms of the clutch element and the arms of the ratchet element 6 slide over one another, during rotation in one direction the arms 6.1 of the ratchet element 6 are disengaged from the teeth 7.1 of the toothed ring, and during rotation in the opposite direction the relative rotation between these elements is blocked. During the rotation in the direction of dose correction, upon disengagement of the arms 6.1 from the teeth 7.1 of the toothed ring 7, the ratchet element 6 rotates under the drive spring force, and then engages the toothed ring 7 again in a position one tooth 7.1 back which corresponds to a correction by one unit. This is because once the arms 6.1 have been moved due to the rotation of the ratchet element 6, they are not deflected anymore by the arms 2.1 of the clutch element.

During the dose setting and the dose correcting the drive element 4 and the piston rod 3 therewith, are immobilized by the above described release mechanism Z via the blocking ring 18. The toothed ring 7 connected with the drive element 4 is also immobilized. The rotation of the control sleeve 13 causes the drive spring 5 to be loaded and the energy to be accumulated therein. During the dose correcting by one unit upon disengagement of the arms 6.1 from the toothed ring 7, the drive spring 5 releases a part of the accumulated energy when the arms 6.1 are moved back by one tooth of the toothed ring 7.

During the dose setting the scale sleeve 12 rotates together with the control sleeve 13 due to their connection preventing relative rotation. The rotation of the control sleeve 13 causes axial translation of the control nut 14 because of the thread connection between them. The scale sleeve 12 takes the axial movement over from the control nut 14, and in consequence the resulting movement of the scale sleeve 12 follows a spiral path enabling the subsequent numbers of the spirally arranged scale 12.1 to be seen in the indication window 8.3. Alternatively, another indication mechanism may be used in the applicator, for example the scale may be located directly on the control sleeve 13. In such a variant, the separate scale sleeve 12 and the control nut 14 are not necessary and such an indication mechanism has a scale arranged circularly. The applicator may also have other elements providing feedback information to the user, such as an indicator confirming an end of injection. Preferably, said indicator may be applied onto the scale sleeve 12 and may be seen upon completion of injection through a separate window provided in the housing 8. A range of operation of the indication mechanism W may be limited in boundary positions by limiting elements known to those skilled in the art. They may operate circumferentially or axially. Depending on a variant of the applicator, the limiting elements may be located on various elements of the dose setting assembly N, the indication mechanism W or on the housing, so as to limit the range of operation of the applicator from an initial position to a maximal dose possible to be set at one time.

In order to trigger an injection of the set dose of a medicament, the user moves the external activating element 16 axially. This causes the projection 16.1 to be disengaged from the blocking ring 18, so that the whole mechanism is no longer blocked and the drive spring 5 may release the accumulated energy. The drive spring 5 rotates the control sleeve 13 and the ratchet element 6, so that the arms 6.1 of the ratchet element 6 push against the teeth 7.1 rotating the toothed ring 7. The drive element 4 and the piston rod 3 rotate with the toothed ring 7. The rotation of the piston rod 3 through the threaded nut 11 causes the piston rod 3 to be translated axially and consequently the cartridge piston is also translated axially causing the set dose of a medicament to be pushed out.

During the injection the scale sleeve 12 and the control nut 14 return to their initial positions due to the rotation of the drive sleeve. When the activating element 16 is triggered by the user, the axial movement of the activating element 16 causes compression of the spring 17. Upon release of the activating element 16 the spring 17 expands causing the activating element 16 to return to its initial position. The projection 16.1 blocks the blocking ring 18 again and the whole mechanism is ready for setting a dose again.

The disclosed drive mechanism has a piston rod 3 that is hollow and provided with an internal thread 3.3, preferably in the form of a track located on the internal surface of the piston rod. Inside the piston rod there is a shaft 21 having an external thread 21.2 cooperating with the internal thread of the piston rod.

During the dose setting and the dose correcting the drive element 4 is blocked against rotation by means of the activating element 16 and the blocking ring 18. The piston rod 3, being rotationally coupled with the drive element 4, does not rotate and remains immobilized. The shaft 21 is rotationally coupled with the clutch element 2 and during the setting of each subsequent dose it rotates in relation to the piston rod 3 moving axially and proximally by a defined distance which corresponds to the set dose (during the dose correcting the shaft 21 rotates in the opposite direction in relation to the piston rod 3 moving axially and distally by the action of the clutch element 2). The position of the shaft 21 upon setting the maximal dose possible to be delivered at one time is shown in FIG. 8*b*. The length of the shaft 21 may be selected so that upon the setting of a maximal dose the shaft 21 contacts the knob 1 so as to prevent further increase of the set dose. Alternatively, the blocking elements preventing axial translation of the shaft 21 during the dose setting may be located on the clutch element 2 or some other mechanism limiting the maximum dose to be delivered at one time may be used.

As during the delivery of each dose the piston rod 3 is rotated and translated distally at the same time, the shaft 21, being engaged with the piston rod 3, rotates together with the piston rod 3 and with the clutch element 2, as well as it is translated distally with the piston rod 3, remaining translated in relation thereto by the mentioned distance corresponding to the delivered dose. Consequently, upon delivery of each subsequent dose the total axial translation of the shaft 21 in relation to the piston rod 3 is increased, while the axial position of the shaft 21 in relation to the clutch element 2 is the same as before the dose was set. This situation is illustrated in FIG. 4*c*. In order to prevent setting of a next dose that could not be delivered due to the limited contents of the cartridge, the mechanism is equipped with blocking elements B located respectively on the piston rod and the shaft. The blocking elements B, shown in particular in FIGS. 5*a*-5*c*, limit the range of the translation of the shaft in relation to the piston rod 3 preventing the possibility to set a next after the last dose of a medicament.

The blocking elements B may consist in particular of the blocking projection 21.1 of the shaft 21, having the blocking surface 21.3 and the blocking projection 3.4 of the piston rod 3, having the blocking surface 3.5. When the volume of a currently set dose is equal to the amount of the medicament remaining in the cartridge, the blocking surfaces 21.3 and 3.5 of the shaft and the piston rod abut each other so as to prevent further increasing of the dose. Upon abutment of the blocking surfaces 21.3 and 3.5 further, the rotation of the threaded shaft 21, hence of the clutch element 2 and the knob 1, is impossible, resulting in that the setting of a dose larger than the amount of the medicament remaining in the cartridge is blocked. On the other hand, upon abutment of the blocking surfaces 21.3 and 3.5 located on the blocking projections 21.1 and 3.4 respectively, reduction of the set dose as well as injection are possible.

In a preferred embodiment of the applicator with the drive mechanism, the drive element 4 is releasably engaged with the dose setting assembly N via a connection with the toothed ring 7; it is also releasably engaged with the release mechanism Z via a connection with the blocking ring 18. This arrangement ensures that, upon disengagement of said connections of the drive element 4 (FIG. 8*b*), the piston rod 3 may be retracted and the cartridge may be replaced by a new one. In order to replace the cartridge, the cartridge enclosure 9 should be disengaged from the nut 11 and the housing 8. The spring 19, which is not pressed anymore, expands and causes the drive element 4 to be pushed away from the toothed ring 7 and disengaged therefrom. The axial translation of the drive element 4 causes it to be disengaged from the blocking ring 18. Consequently, the drive element 4 may be rotated so that the piston rod 3, being engaged with the drive element 4 rotates as well. This enables the piston rod 3 to be retracted to its initial position by its rotation in the nut 11. While the piston rod 3 is being retracted, the shaft 21 which is blocked against rotation by its engagement with the clutch element 2, remains immobilized and therefore, the axial position of the piston rod 3 in relation to the shaft 21, after the piston rod 3 has been retracted, returns to the initial state. When the cartridge enclosure 9 is being engaged again with the nut and the housing 18, the relative axial movement of these elements causes translation of the pushrod 20 which is pressed by the cartridge enclosure 9. The pushrod 20 exerts pressure on the drive element 4 which is therefore translated axially exerting pressure on the spring 19. The translation of the drive element 4 causes it to get engaged again with the blocking ring 18 and with the dose setting assembly N via the toothed ring 7, and the applicator is ready to be used.

In the alternative embodiment, in which the applicator is disposable, the drive element 4 may be integral with the toothed ring 7.

FIG. 9 shows a longitudinal section of a fragment of an alternative applicator provided with the disclosed drive mechanism. In the applicator according to this embodiments, any known in the art dose setting assembly and indication mechanism may be used. In particular, the dose setting assembly and the indication mechanism may have the form as in the embodiment shown in FIGS. 1-8. In the current embodiment shown in FIG. 9, the drive mechanism is equipped among others with a drive element 104.

The applicator further comprises an external activating element 116 cooperating with a blocking sleeve 118. The blocking sleeve 118 is axially movable; the external activating element 116 and the blocking sleeve 118 constitute together a release mechanism Z'. The blocking sleeve 118 is coupled with a toothed ring 107, preferably by means of the cooperating circumferential projections and indents. Before axial movement of the external activating element 116, the blocking sleeve 118 prevents rotation of the toothed ring 107, so that in consequence the whole mechanism is blocked and the setting and/or correction of a dose is prevented. The drive element 104 is connected with the toothed ring 107, preferably by means of cooperating circumferential projections and indents, so that these elements are not rotated during the setting and/or correction of a dose, and they rotate during the injection. The delivery of a medicament is initiated by an axial movement of the external activating element 116 which in turn exerts pressure on a projection 118.1 and moves axially the blocking sleeve 118. In consequence of this translation the blocking sleeve 118 is disengaged from the toothed ring 107 and the whole mechanism gets unlocked enabling the energy accumulated in the drive spring to be released and the set dose to be delivered. While the injection is being triggered, a shelf 188.2 of the blocking sleeve 118 is moved exerting pressure on a spring 119 so that the latter is compressed. Upon release of the external activating element 116, the energy accumulated in the spring 119, during the translation the activating element 116 and the blocking sleeve 118, is released. The spring 119 then exerts pressure on the blocking sleeve causing it to return to its initial position and re-engagement with the toothed ring 107, blocking the whole mechanism which is ready for setting a dose again.

In the variant where the applicator is disposable and the cartridge replacement is possible, the spring 119 is compressed while the cartridge enclosure is being connected with the housing. In this case, when the blocking sleeve 118 is being translated, the spring 119 is additionally pressed. Upon the release of the external activating element 116, not all the accumulated elastic energy is released, but only the part accumulated in consequence of the pressure exerted by the blocking sleeve 118.

In order to replace the medicament cartridge, the cartridge enclosure is disengaged from the housing which causes the energy of the spring 119 to be released so that it exerts pressure on a pushrod 120. The pushrod 120 is connected with the drive element 104 in such a way that these elements may be rotated in relation to each other but they are coupled axially, preferably by means of a clip comprising a projection 120.1 and an indent 104.1 of the drive element. The pressure of the spring 119 makes the pushrod 120 and the drive element 104 to be moved axially in the distal direction. Consequently, the drive element 104 gets disengaged from the toothed ring 107 may be freely rotated enabling the piston rod to be retracted. The cartridge enclosure, when re-engaged with the housing, exerts pressure on the pushrod 120 translating it in the proximal direction. This translation causes the spring 119 to be compressed again and the drive element 104 to be translated and re-engaged with the toothed ring 107.

FIG. 10 shows a longitudinal section of another embodiment of the applicator provided with the disclosed drive mechanism.

In this embodiment, the activating element consists of a button 216 located at the proximal end of the applicator. The button 216 is axially coupled with a button sleeve 216A, preferably by means of a connection comprising an indent and a peripheral projection.

During the dose setting the clutch element 202 is rotated by means of a knob 201 with which it is rotationally coupled. The clutch element 202 is also connected with a toothed ring 207. The toothed ring 207 comprises a toothed flange, and the clutch element comprises teeth that pass subsequent positions on the toothed flange during the dose setting. The teeth of the clutch element may operate axially or radially and they may have a form of ratchet arms. The applicator with the button 216 located proximally may also be equipped with another known in the art dose setting assembly or the dose setting assembly shown in FIGS. 1-8. During the dose setting a drive sleeve 213 and a drive spring 205 are rotated, so that elastic energy is accumulated in the drive spring 205. The drive spring 205 is connected with the drive sleeve 213 at one side and with a spring blocking 215 at the other side.

Alternatively, the drive spring 205 may be connected with the clutch element 202, its other end being fixed directly in the housing. During the dose setting the mechanism is blocked by means of the connection between the toothed ring 207 and the clutch element 202. These two elements are advantageously pressed against each other by means of a spring 219. The button sleeve 216A is releasably connected to the clutch element 202 and remains immobilized during the dose setting. The volume of a currently set dose is indicated on a scale sleeve 212. The applicator according to this embodiment may also be equipped with a different indication mechanism known in the art. During the dose correction, the clutch element 202 is rotated in a direction opposite to that of the dose setting. The teeth of the clutch element 202 pass to subsequent positions on the toothed flange 207 but in the opposite order than during the dose setting. During the dose correction, the energy accumulated in the drive spring 205 which in this embodiment is a torsional spring.

In order to initiate the dose delivery, a user presses the button 216 causing the button sleeve 216A to be moved axially. During this translation the button sleeve 216A gets engaged with the clutch element 202 and exerts pressure on the toothed ring 207 translating it axially in the distal direction. When the teeth of the toothed ring 207 and those of the clutch element 202 are disengaged, the mechanism is unlocked and the drive spring 205 may release the accumulated energy causing the components of the mechanism to return to their initial positions. The button sleeve 216A is rotationally engaged with a piston rod 203 e.g. by means of the splines or cooperating flattened surfaces. In this described embodiment the button sleeve 216A functions as a drive element. During the dose delivery, the button sleeve 216A is rotationally engaged with the clutch element 202 and it rotates under the force of the drive spring 205. This causes the piston rod 203 to be screwed out through a threaded nut 211. Upon release of the button 216, a spring 217 located between the button 216 and the knob 201, expands making the button return to its initial position while the spring 219 presses the toothed ring 207 against the clutch element 202 and blocks the mechanism again, so that it is ready for setting a dose again.

The last dose blocking is realized by cooperation of a threaded shaft 221 located inside the piston rod 203 having an internal thread. The shaft 221 is rotationally coupled with the clutch element 202 via a connection element 222. During the dose setting, rotation of the clutch element 202 makes the shaft 221 rotate, and the shaft 221 is screwed out in the proximal direction, being also translated in relation to the piston rod 203. During the dose correction, the shaft 221 is translated in the distal direction. During the dose delivery, the shaft 221 is rotated and translated axially together with the piston rod 203 and their relative position is not changed. The position of the shaft 221 in relation to the piston rod 203 corresponds to a sum of the doses delivered from the cartridge and the dose currently set. When the currently set dose equals the amount of a medicament remaining in the cartridge, the movement of the shaft 221 in relation to the piston rod 203 is blocked by means of blocking elements, advantageously located on these elements and the user is not able to increase the dose anymore because the clutch element 202 may not be further rotated.

If the applicator is configured as a reusable device, the user may replace the cartridge by a new one. The applicator has a disengagement element 223 and a toothed ring 224 which is blocked against rotation in the housing. The disengagement element 223 is rotationally coupled with the button sleeve 216A and it is connected with the toothed ring 224 in such a way that it may be rotated in relation to the toothed ring 224 in one direction. During the dose setting, the disengagement element is rotated together with the button sleeve 216A. Disengagement of the cartridge enclosure from the housing causes the spring 219 to expand and the disengagement element 223 to be disconnected from the button sleeve 216A. The button sleeve 216A may be freely rotated which enables the piston rod 203 to be screwed back into the housing. At the same time, the threaded shaft 221 is moved to its initial position allowing the last dose blocking mechanism to be reset.

The invention claimed is:

1. A drive mechanism for an applicator for delivering a dose of a medicament, comprising:

a dose setting assembly, a knob, a rotatable and axially non-translatable clutch element coupled in rotation with the knob and cooperating with the dose setting assembly, a rotatable piston rod having an external thread, the piston rod being located inside the clutch element, a drive element and a drive spring, wherein when a dose is being set by rotation of the knob, the clutch element is rotated so that the drive spring is loaded, while the drive element and the piston rod are immobilized, and when the dose is being delivered, the drive spring is being released causing the drive element to rotate together with the piston rod, the piston rod being translated axially in a distal direction, wherein the piston rod is hollow and has an internal thread, a shaft having an external thread for cooperation with the internal thread of the piston rod is located within the piston rod, the shaft being coupled in rotation with the clutch element so that during the setting of each subsequent dose the shaft is rotated in relation to the piston rod and moved axially in a proximal direction, while during the delivery of the dose the shaft is immobilized in relation to the piston rod, and wherein the total translation of the shaft in relation to the piston rod caused by the setting of a defined number of doses is limited by of blocking elements located respectively on the piston rod and the shaft.

2. The mechanism according to claim 1, wherein the shaft is engaged in rotation with the clutch element by means of longitudinal splines.

3. The mechanism according to claim 1, wherein the blocking elements consist of respectively a projection located on the internal thread of the piston rod and a projection located on the external thread of the shaft, the blocking elements being adapted to block the rotation of the piston rod in relation to the shaft.

4. The mechanism according to claim 1, wherein the drive element has an orifice of a non-circular cross-section, the piston rod has a cross-section with a non-circular contour corresponding to the non-circular cross-section of the orifice of the drive element.

5. An applicator for delivering a dose of a medicament, comprising:

a housing a cartridge enclosure adapted to receive a medicament containing cartridge, a dose setting assembly, a knob, a rotatable and axially non-translatable clutch element coupled in rotation with the knob and cooperating with the dose setting assembly, a rotatable piston rod having an external thread, the piston rod being located inside the clutch element, a drive element and a drive spring, wherein when a dose is being set by the knob, the clutch element is rotated so that the drive spring is loaded, while the drive element and the piston rod are immobilized, and when the dose is being delivered, the drive spring is being released causing the drive element to rotate together with the piston rod, the piston rod being moved axially in a distal direction, wherein the piston rod is hollow and has an internal thread and a shaft having an external thread for cooperation with the internal thread of the piston rod is located within the piston rod, the shaft being engaged in rotation with the clutch element so that during the setting of each subsequent dose the shaft is rotated in relation to the piston rod and moved axially in a proximal direction, while during the delivery of the dose the shaft is immobilized in relation to the piston rod, and wherein the total translation of the shaft in relation to the piston rod caused by the setting of a defined number of doses is limited by means of blocking elements located respectively on the piston rod and the shaft.

6. The applicator according to claim 5, wherein the drive element has an orifice of a non-circular cross-section, the piston rod has a cross-section with a non-circular contour corresponding to the non-circular cross-section of the orifice of the drive element.

7. The applicator according to claim 5, wherein the drive element is releasably coupled with the dose setting assembly.

8. The applicator according to claim 5, wherein the blocking elements comprise respectively a projection located on the internal thread of the piston rod and a projection located on the external thread of the shaft, the blocking elements being adapted to block the rotation of the piston rod in relation to the shaft.

9. The applicator according to claim 5, further comprising an indication mechanism comprising a control sleeve, a scale sleeve and a control nut, the control sleeve having an external thread for cooperation with the control nut, the control nut being blocked against rotation in the housing and axially movable therein, the control nut being also axially engaged with the scale sleeve, which is moved along a spiral path during the dose setting and the dose correcting.

10. The applicator according to claim 9, wherein the indication mechanism comprises an indication window showing the currently set dose.

11. The applicator according to claim 5, wherein the drive spring is a torsional spring.

12. The applicator according to claim 5, further comprising a release mechanism adapted to be in a locked state or in an unlocked state, the release mechanism comprising an external activating element, wherein when the release mechanism is in the locked state, the drive element may not rotate, and when the release mechanism is in the unlocked state, the drive element may rotate, the release mechanism being adapted to be switched from the locked state to the unlocked state by a user.

13. The applicator according to claim 12, wherein the external activating element consists of a trigger located on a side wall of the housing, the trigger being blocked against rotation and axially translatable.

* * * * *